(12) United States Patent
Mandelis et al.

(10) Patent No.: US 7,729,734 B2
(45) Date of Patent: Jun. 1, 2010

(54) NON-INVASIVE BIOTHERMOPHOTONIC SENSOR FOR BLOOD GLUCOSE MONITORING

(76) Inventors: Andreas Mandelis, 3 Scarborough Heights, Toronto, Ontario (CA) M1M 2V3; Sergey Telenkov, 11035 NW. 39-th St., Apt.305, Sunrise, FL (US) 33351

( * ) Notice: Subject to any disclaimer, the term of this patent is extended or adjusted under 35 U.S.C. 154(b) by 1103 days.

(21) Appl. No.: 11/368,698

(22) Filed: Mar. 7, 2006

(65) Prior Publication Data
US 2007/0213607 A1    Sep. 13, 2007

(51) Int. Cl.
*A61B 5/145* (2006.01)
(52) U.S. Cl. ..................................... 600/316
(58) Field of Classification Search ............. 600/316, 600/322, 365; 356/39
See application file for complete search history.

(56) References Cited

U.S. PATENT DOCUMENTS

| | | | | |
|---|---|---|---|---|
| 5,553,616 | A * | 9/1996 | Ham et al. | 600/316 |
| 5,896,198 | A * | 4/1999 | Chou et al. | 356/484 |
| 6,709,857 | B2 * | 3/2004 | Bachur, Jr. | 435/288.7 |
| 2004/0135085 | A1 * | 7/2004 | Trofimov et al. | 250/339.11 |
| 2004/0225206 | A1 * | 11/2004 | Kouchnir | 600/316 |
| 2005/0137469 | A1 * | 6/2005 | Berman et al. | 600/316 |

* cited by examiner

*Primary Examiner*—Eric F Winakur
*Assistant Examiner*—Etsub D Berhanu
(74) *Attorney, Agent, or Firm*—Lynn C. Schumacher; Hill & Schumacher

(57) ABSTRACT

There is provided a glucose monitoring method and apparatus based on the principle of Wavelength-Modulated Differential Laser Photothermal Radiometry (WM-DPTR). Two intensity modulated laser beams operating in tandem at specific mid-infrared (IR) wavelengths and current-modulated synchronously by two electrical waveforms 180 degrees out-of-phase, are used to interrogate the tissue surface. The laser wavelengths are selected to absorb in the mid infrared range (8.5-10.5 µm) where the glucose spectrum exhibits a discrete absorption band. The differential thermal-wave signal generated by the tissue sample through modulated absorption between two specific wavelengths within the band (for example, the peak at 9.6 and the nearest baseline at 10.5 µm) lead to minute changes in sample temperature and to non-equilibrium blackbody radiation emission. This modulated emission is measured with a broadband infrared detector. The detector is coupled to a lock-in amplifier for signal demodulation. Any glucose concentration increases will be registered as differential photothermal signals above the fully suppressed signal baseline due to increased absorption at the probed peak or near-peak of the band at 9.6 µm at the selected wavelength modulation frequency. The emphasis is on the ability to monitor blood glucose levels in diabetic patients in a non-invasive, non-contacting manner with differential signal generation methods for real-time baseline corrections, a crucial feature toward precise and universal calibration (independent of person-to-person contact, skin, temperature or IR-emission variations) in order to offer accurate absolute glucose concentration readings.

24 Claims, 3 Drawing Sheets

NON-INVASIVE BIOTHERMOPHOTONIC SENSOR FOR BLOOD GLUCOSE MONITORING

FIELD OF INVENTION

The present invention relates to a method and device to monitor blood glucose in diabetic patients in a non-invasive manner.

BACKGROUND OF THE INVENTION

The metabolic disease known as diabetes mellitus afflicts a large and growing number of people worldwide. In order to manage this health condition, frequent monitoring of blood glucose level is essential, especially for the patients who require regular insulin injections. To reduce risk of severe long-term health complications, it is recommended that diabetes patients check blood sugar level up to five times a day to maintain physiological glucose concentration between 90 and 120 mg/dl [A. C. Guyton and J. E. Hall, Textbook of medical physiology $10^{th}$ ed. Philadelphia, Ch. 78 (2000)]. The standard technique for measurement of glucose concentration requires skin puncture to draw a small blood sample (typically microliter volume) which can be examined using a test strip and automated meter to report the results. Although this technique provides accurate glucose concentration data, frequent skin puncture is associated with significant discomfort, pain and risk of infection. Besides, it cannot be used for continuously monitoring glucose levels, an essential requirement especially for some categories of diabetics, including juvenile diabetes. Continuous monitoring also enables the creation of a real-time insulin pump—a much sought after mode of insulin delivery that better mimics the normal physiological condition. Over the past two decades, search for alternative methods of glucose monitoring resulted in development of a number of optical technologies including an IR absorption technique [H. Zeller, P. Novak and R. Landgraf, Int. J. Art. Org. 12, 129 (1989)], the pulsed photoacoustic method [H. A. MacKenzie, H. S. Ashton, S. Spiers, Y. Shen, S. S. Freeborn, J. Hannigan, J. Lindberg and P. Rae Clinical Chem. 45, 1587 (1999); K. M. Quan, G. B. Christison, H. A. MacKenzie and P. Hodgson, Phys. Med. Biol. 38, 1911 (1993)], polarimetry [G. L. Cote, M. D. Fox and R. B. Northrop, IEEE Trans. Biomed. Eng. 44, 1221 (1992)] and Raman spectroscopy [A. J. Berger, Y. Wang and M. S. Feld, Appl. Opt. 35, 209 (1996)].

Despite significant effort directed towards the development of non-invasive and minimally-invasive techniques for glucose monitoring [O, S. Khalil, Clinical Chem. 45, 165 (1999); G. L. Cote and R. J. McNichols, Biomedical Photonics Handbook, Ed.: Tuan Vo-Dinh, Ch. 18 (CRC Press) (2003)], no completely non-invasive sensor satisfying sensitivity and specificity conditions similar to intrusive sensors is available at the moment. [R. W. Waynant and V. M. Chenault (April 1998), "Overview of Non-Invasive Fluid Glucose Measurement Using Optical Techniques to Maintain Glucose Control in Diabetes Mellitus", at http://www.ieee.org/organizations/pubs/newsletters/leos/apr98/overview.htm (LEOS Newsletter, Vol. 12)]. Traditionally, the near-IR spectral range (0.8-3 µm) has been explored for the development of optical technologies for glucose monitoring because of relatively low water absorption [M. Robinson, R. P. Eaton, D. M. Haaland, D. W. Koepp, E. V. Thomas, B. R. Stallard, and P. L. Robinson, Clin. Chem. 38, 1618 (1992); M. A. Arnold and G. W. Small, Anal. Chem. 62, 1457 (1990); D. Kajiwara, T. Uemura, H. Kishikawa, K. Nishida, Y. Hashiguchi, M. Uehara, M. Sakakida, K. Ilchinose and M. Shichiri, Med. Biol. Eng. Comput. 31, S17 (1993); R. Marbach, Th. Koschinsky, F. A. Gries and H. M. Heise, Appl. Spectrosc. 47, 875 (1993)]. Quantitative interpretation of spectroscopic data in the near-IR often requires sophisticated processing algorithms due to overlap of glucose molecule overtones and absorption bands of other tissue analytes. Farther into the mid-IR region (2.5-10 µm), the spectrum of anhydrous glucose has more than 20 absorption peaks, not all of which are specific to this molecule. Of particular significance, however, is the prominent absorption peak in the 8.5-10.5 µm band which is due to the carbon-oxygen-carbon bond in the pyrane ring of glucose. This feature is peaked at ca. 9.7 µm, and is isolated from other interfering peaks in human blood [C. J. Pouchert, The Aldrich Library of Infrared Spectra, 3rd. ed., Aldrich Chemical Co. (1981)]. This peak is within the spectral range of the $CO_2$ laser which emits at several discrete wavelengths between 9.2 and 10.8 µm. A major difficulty for practical monitoring of glucose in human tissue within this spectral range is the intrinsic high-background absorption coefficient of water (640 $cm^{-1}$ at 9.7 µm), which tends to fully dominate the relatively low normal concentration of glucose in human blood (typically 90 to 120 mg/dl). Nevertheless, a modulated $CO_2$ laser emission at 9.6 µm and a multiple attenuated total reflection (ATR) plate, both sides of which were immersed in the sample solution for signal enhancement (unrealistic for practical devices), was successfully used in obtaining definite correlations between ATR signal and glucose concentration in the range of 50-280 mg/dl [Y. Mendelson, C. Clermont, R. A. Peura and B-C. Lin, IEEE Trans. Biomed. Eng. 37, 458 (1990)]. Unfortunately, the data scatter in the critical 50 to 120 mg/dl range was on the order of 50-90% which is unacceptable for a practical device implementation. Several factors contributed to this: ATR plate heating, high signal sensitivity to the angle of incidence of the laser beam on the plate, the inherent depth inadequacy of the evanescent electromagnetic (EM) field probing only ca. 1.3 µm into the adjacent fluid zone, and the small, yet interfering, background absorptions (e.g. proteins) which cannot be eliminated using single-ended optical techniques. Besides, any practical implementation of this method would stumble on serious difficulties with regard to signal variations due to contact interface variations of the ATR prism from patient to patient and the presence of the glucose-deficient tissue surface epidermis layer (~80 µm).

SUMMARY OF THE INVENTION

The present invention provides a non-invasive glucose monitoring apparatus ("Spectroscopic Glucose Radiometer—SGR") based on a modality utilizing Wavelength-Modulated Differential Laser Photothermal Radiometry (WM-DPTR). In one aspect, the present invention comprises a glucose detection method comprising the steps of:

a) providing first and second sources of radiation, the first and second sources generating first and second beams, respectively, wherein the first source of radiation has a wavelength approximately equal to a peak wavelength of a glucose absorption band, and wherein the second source of radiation has a wavelength off of the peak of the glucose absorption band;

b) producing a first modulated beam and a second modulated beam by modulating an intensity of the first beam and an intensity of the second beam, respectively; wherein the first and second modulated beams are modulated at a substantially equal frequency, and wherein a phase of the first modulated beam differs from a phase of the second modulated beam by approximately 180°;

c) substantially equalizing an intensity of the first modulated beam and an intensity of the second modulated beam;

d) directing the first and second modulated beams to co-linearly irradiate a tissue;

e) obtaining a signal by detecting emission radiated by the tissue with a phase-sensitive detection system comprising a thermal detector, wherein a reference signal for the phase-sensitive detection is provided at the frequency; and f) correlating the signal with a concentration of glucose in the tissue.

In another aspect of the invention, there is provided an apparatus for detecting glucose, the apparatus comprising:

a) first and second sources of radiation, the sources generating first and second beams, respectively, wherein the first source of radiation has a wavelength approximately equal to a peak wavelength of a glucose absorption band, and wherein the second source of radiation has a wavelength off of the peak of the glucose absorption band;

b) modulation means for modulating an intensity of the first beam and an intensity of the second beam, wherein the modulation means is adapted to modulate the first and second beams at a substantially equal frequency, the modulation means being further adapted to produce a difference in phase between the first and second modulated beams of approximately 180 degrees;

c) equalizing means for substantially equalizing a power of the first modulated beam and the second modulated beam;

d) optical means for directing the first and second modulated beams to co-linearly irradiate a tissue:

e) collection means for collecting thermal power radiated by the tissue;

f) a phase-sensitive detection system comprising a thermal detector adapted to detect the collected thermal power, the phase-sensitive detection system receiving as an input a reference signal at the frequency; and g) means for recording and processing the signal.

1) irradiating the tissue surface with two specialty low-power (~200 mW) radiation emitting sources ($CO_2$ lasers or other appropriate sources).

2) operating the said sources in tandem and modulated synchronously at angular modulation frequency $\omega=2\pi f$ with f in the 0.1-10000 Hz range by two electrical waveforms 180 degrees out-of-phase.

3) producing periodic frequency pulses of the irradiating sources (laser beams) in the range covering 0.1 Hz to 10 kHz, especially in the vicinity of (but not confined to) 700 Hz.

4) making the two spatially separated beams at the desired wavelengths co-incident on the sample surface using appropriate optical elements.

5) equalizing the intensities of the two beams via a neutral density filter and monitoring sub-surface tissue fluid differential absorption at the pre-determined wavelengths in the presence of glucose concentration within the normal human range (90-120 mg/dl) in order to determine the healthy band for normal residual glucose of the emissive infrared signal and/or adjust the said signal to zero to null the differential absorption from the healthy band.

6) generating out-of-phase photothermal-wave signals at both wavelengths leading to minute changes in net sample temperature (<1K) due to differential absorption.

7) using photothermal-wave superposition (destructive interference) over one modulation period in the tissue leading to net differential blackbody radiation emission at the said two wavelengths.

8) collecting said emission signal with suitable mid-IR collecting optics including solid-angle and reflectivity optimized curved mirrors and specialty fiber-optic delivery systems (e.g. silver halide optical fibers).

9) detecting said collected signal with a wide-bandwidth (dc-MHz) cryogenic broadband HgCdTe (MCT) detector (2-12 µm), or any other solid-state detector in the mid-IR capable of fast signal modulation, such as room-temperature or thermoelectrically-cooled HgCdZnTe detector (2-6 µm), ZnSe, Ge, or other commercially available or specially designed and engineered detectors. This list is understood not to be exclusive but inclusive of any current or future state-of-the art mid-IR detector device.

10) outfitting the said detector with a narrow bandpass IR filter to block the $CO_2$ laser emission line range, if so required by possible overlap of the spectral bandwidth of the detector with the source emission range.

11) demodulating the said detector signal by an appropriate demodulating device (lock-in amplifier)

12) recording the signals by a computer 13) processing said recorded signal and correlating it to glucose concentration.

BRIEF DESCRIPTION OF THE DRAWINGS

The device for monitoring blood glucose according to the present invention will now be described by way of example only, reference being had to the accompanying drawings in which.

DETAILED DESCRIPTION OF THE INVENTION

The present invention provides a device based on non-invasive, non-contacting measurements with differential signal generation methods for real-time baseline corrections, a crucial feature toward precise and universal calibration (independent of person-to-person mid-IR spectral baseline variations, skin and subcutaneous absorption, body temperature or IR-emission variations) in order to offer accurate absolute glucose concentration readings. In addition, spectroscopic baseline suppression, coupled to maximally high signal dynamic range afforded by differential lock-in amplifier detection, is very promising for detection of both hyperglycemia and hypoglycemia.

Figure 1:
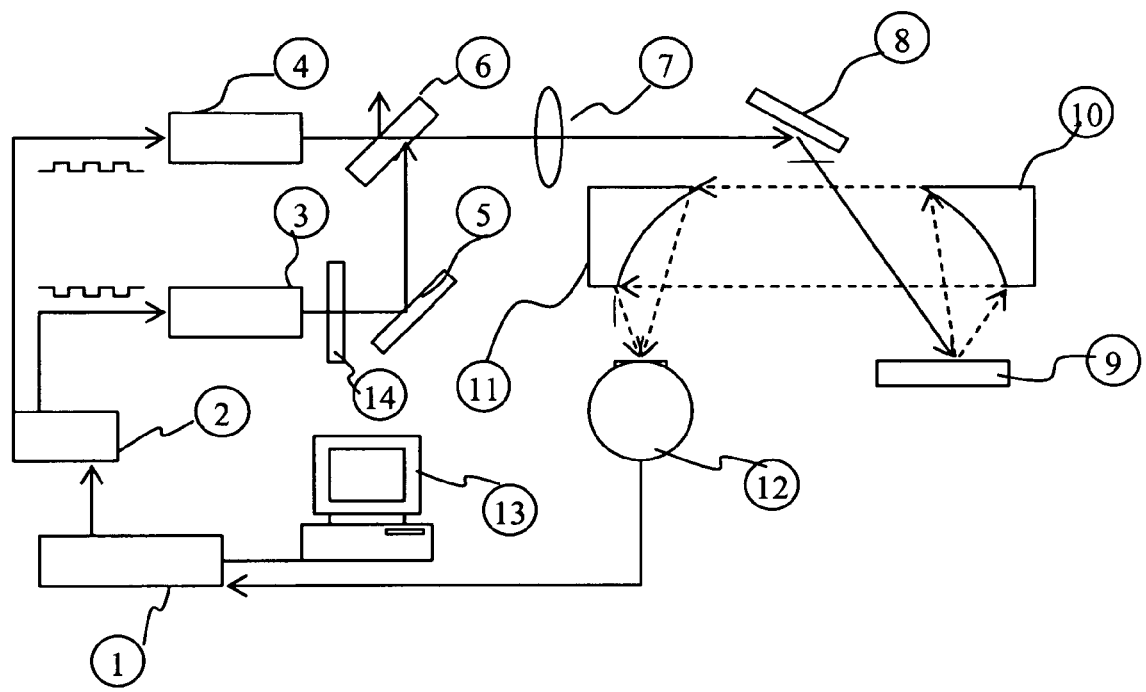
FIG. 1 illustrates a schematic diagram of an embodiment of the Spectroscopic Glucose Radiometer.

FIG. 1 shows an embodiment of the apparatus for non-invasive glucose monitoring, using two specialty low-power (~200 mW) $CO_2$ lasers 3 and 4. Alternatively, the sources may be two spectrally-filtered halogen lamps, preferably low-power specialty lamps with a power of approximately 200 mW. The lamps are preferably spectrally filtered to spectral bands near 9.6 μm and 10.7 μm. The lasers are operating in tandem and are current-modulated synchronously at modulation frequency $f=\omega/2\pi$ in the 0.1-10000 Hz range by out-of-phase electrical waveforms generated by a wave generator 2. Alternatively, the two beams may be modulated by mechanical choppers 180 degrees out of phase, opto-acoustic modulators 180 degrees out of phase, or by electo-optical modulators 180 degrees out of phase. The two spatially separated laser beams at the desired wavelengths are made coincident by directing the beams through mirror 5, beam combiner 6, lens 7 and mirror 8 on the sample surface 9 as shown in FIG. 1. Alternatively, the two beams may be directed towards the sample using optical fibers fitted with a beam combiner and an optical lens at the tip of each fiber. The intensities of the beams are equalized by a variable neutral density filter 14 or by current adjustment of one of the two laser power supplies. The beams are modulated at the same frequency but 180 degrees out-of-phase. This wavelength modulation arrangement gives rise to destructive interference over one modulation period between the two thermal waves generated through optical absorption at the two chosen wavelengths at the peak and trough (baseline) of the glucose 8.5-10.5 μm absorption band. This amounts to a differential thermal-wave signal generated in the tissue sample. Thermal waves are minute oscillatory changes of sample temperature (<1 K) leading to differential blackbody radiation emission modulated at the common frequency of the wavelength modulation. The emission is collected by paraboloidal mirrors 10 and 11 and measured with a broadband HgCdTe (MCT) detector 12 (2-12 μm bandwidth) outfitted with a narrow bandpass IR filter to block the $CO_2$ laser emission line range. Alternatively, the emission may be collected with solid angle and reflectivity optimized curved mirrors or a mid-IR collecting fiber optic system. It is to be understood that other clinically convenient embodiments of the mid-IR detector and blackbody emission power can be substituted for the aforementioned devices within the scope of the invention. These comprise, but are not limited to, fiber optic delivery systems (e.g. Silver halide mid-IR fibers), room-temperature or thermoelectrically-cooled HgCdZnTe (MCZT) detector (2-6 μm), ZnSe, Ge, or other commercially available or specially designed and engineered detectors. The MCT detector 12 is coupled to a lock-in amplifier 1 for signal demodulation, referenced at the wavelength modulation frequency $f=\omega/2\pi$. The demodulated signal from the lock-in amplifier 1 is sent to a personal computer 13 for recording, processing, or to another storage and display device. If the intensities of the two beams are properly equalized a zero signal is expected from equal (background) absorption coefficients at the two wavelengths in the absence of any glucose concentration. Normal physiological glucose concentration range signals (90-120 mg/dl) lead to a healthy differential thermal-wave signal calibration band recorded by the lock-in amplifier. Any glucose concentration increases are registered as excess photothermal signals above the healthy base band, the said healthy base band signals possibly been fully suppressed. Differential signals as a result of increased absorption at 9.6 μm at a modulation frequency in the range between 0.1 Hz and 10 kHz, are judiciously selected near the peak and baseline of the absorption band in FIG. 2 so as to maximize the differential photothermal-wave signal.

The biothermophotonic device relies on judiciously chosen differential $CO_2$ laser line absorption in tissue in the 8.5-10.5 μm glucose IR absorption band, thermal-wave generation in tissue and dual wavelength phase-sensitive detection of radiometric signals (detection of photothermal blackbody photons) in the mid-IR spectral band away from the absorption region. The spectrally differential thermal-wave signal of the mid-IR response recorded at the peak and off-peak of glucose absorption can be related to glucose concentration in the tissue specimen. This biosensor device may be applied for measurements of glucose concentration in the interstitial fluid (ISF) of the superficial skin layers to establish correlation with glucose concentration in the blood. Since it measures only one absorption band through its own generated infrared emissions at two infrared absorption locations (maximum and minimum), the biosensor is self referenced, featuring real-time baseline normalization, and in relative isolation from interfering tissue absorptions. Therefore, it can yield absolute measurements of glucose concentration within, below or above the healthy base-band, unlike many other optical and near-IR techniques introduced to-date [M. Robinson, R. P. Eaton, D. M. Haaland, D. W. Koepp, E. V. Thomas, B. R. Stallard, and P. L. Robinson, *Clin. Chem.* 38, 1618 (1992); M. A. Arnold and G. W. Small, *Anal. Chem.* 62, 1457 (1990); D. Kajiwara, T. Uemura, H. Kishikawa, K. Nishida, Y. Hashiguchi, M. Uehara, M. Sakakida, K. Ilchinose and M. Shichiri, *Med. Biol. Eng. Comput.* 31, S17 (1993); R. Marbach, Th. Koschinsky, F. A. Gries and H. M. Heise, *Appl. Spectrosc.* 47, 875 (1993)].

This differential method will give at least one order-of-magnitude higher signal resolution and signal-to-noise ratio increase over conventional single-ended optical methods [C. H. Wang and A. Mandelis, Rev. Sci. Instrum. 71, 1961 (2000)] and thus yield resolution superior to existing optical methods within the physiological glucose concentration range. The separation of source and detection wavelengths is also very important in providing effective isolation of the glucose peak with minimum interferences from nuisance absorptions including interference from the incident laser beams. In future in-vitro or in-vivo tissue applications, the frequency-dependent thermal penetration depth can be adjusted through appropriate frequency tuning to maximize the differential signal collected from subsurface depths well beyond the epidermis layer: from dermis (>500 μm) and from interstitial fluid or blood layers. This is an important feature of thermal-wave based methods, as the strong water absorption will allow effective optical penetration down to only 20-30 μm inside the glucose containing layers below the epidermis. It is important to emphasize that the differential spectroscopic scheme of signal generation of this device subtracts out automatically the strong water absorption baseline (640 $cm^{-1}$ at 9.7 μm). The power of laser irradiation will be strictly controlled and maintained within regulatory-body-approved safe exposure level at all times.

Figure 2:
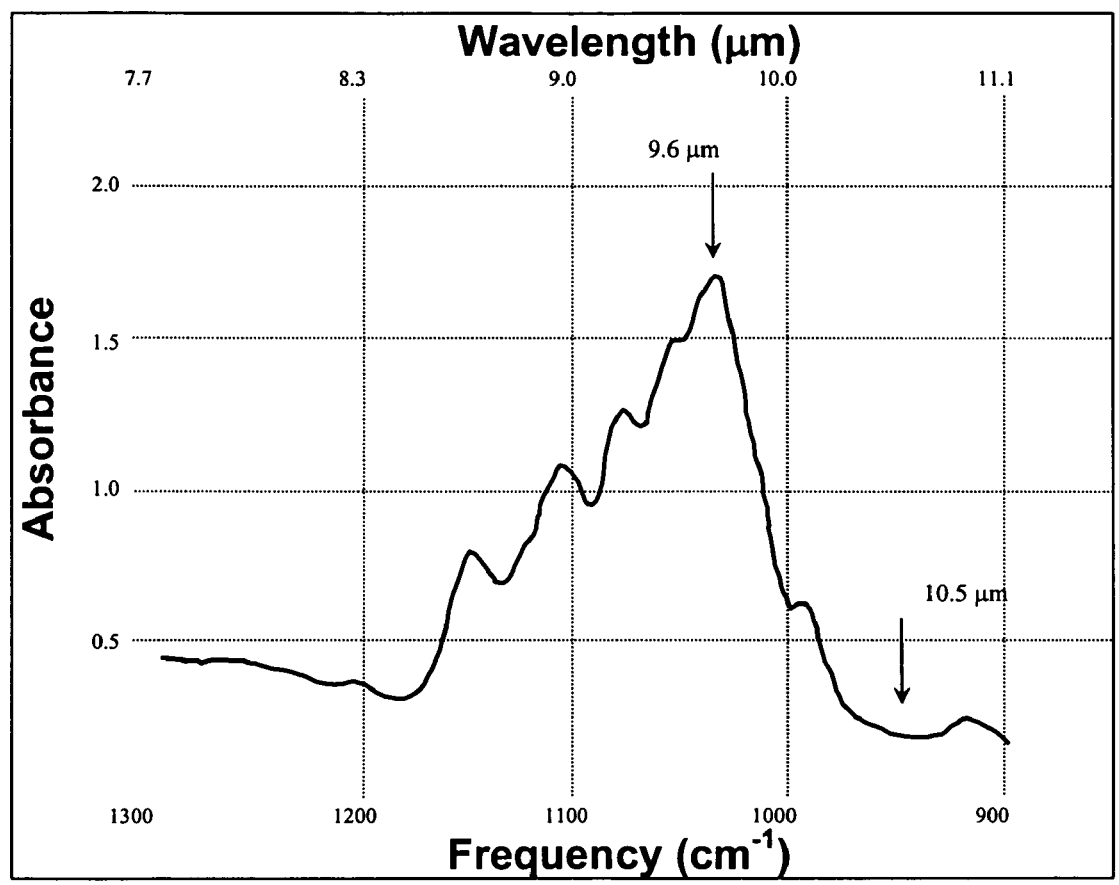
FIG. 2 illustrates a section of the mid-IR absorption spectrum of glucose showing the two proposed detection wavelengths.
Figure 3:
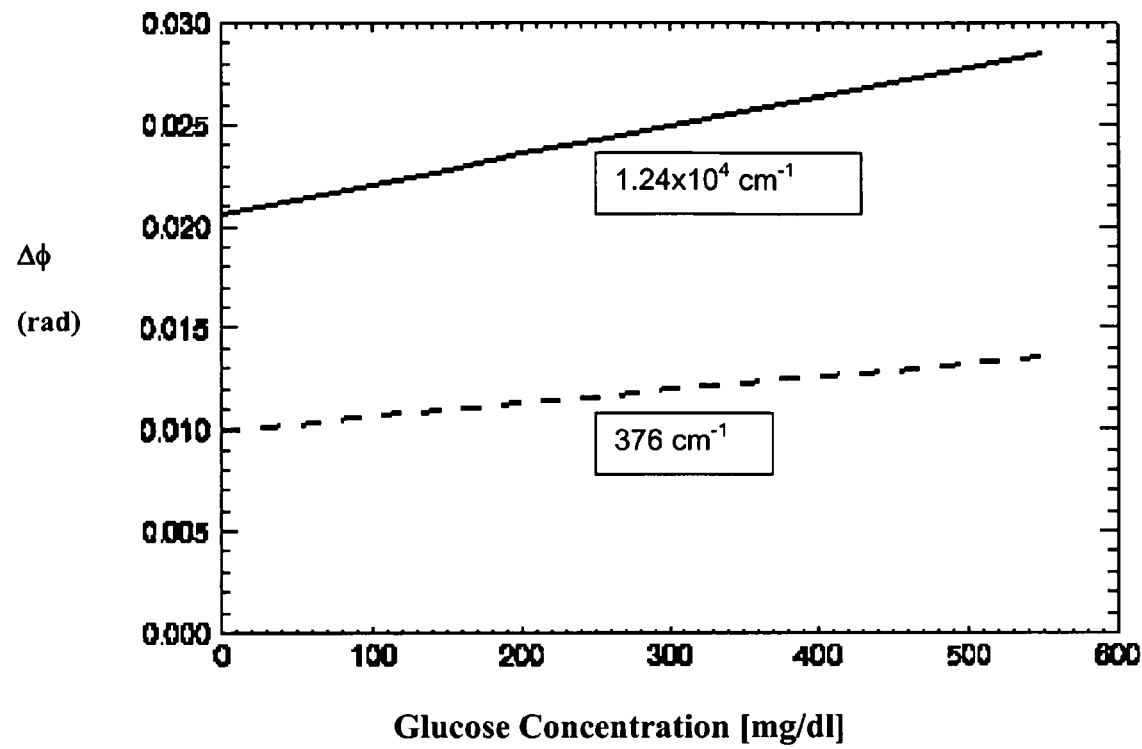
FIG. 3 illustrates differential photothermal-wave phase as a function of glucose concentration for $\alpha=1.24\times10^4$ cm$^{-1}$ (modulation frequency 70 Hz) and $\alpha=376$ cm$^{-1}$ (modulation frequency 30 Hz). These are values of optical absorption coefficient corresponding to the peak of glucose band and to human skin, at wavelengths 9.6 µm and 10.5 µm, respectively (FIG. 2).

Theory of Spectroscopic Differential Radiometry with Applications to Glucose Detection The SGR instrument is based on Wavelength-Modulated Differential Laser Photothermal Radiometry (WM-DPTR). It takes advantage of characteristic spectral features of glucose (spectral "fingerprints") in the mid-IR spectral range (8.5-12 μm). The glucose absorption spectrum has several fundamental absorption bands in the mid-IR that can be used to distinguish glucose molecules from other tissue analytes. Specifically, the absorption peak at 9.6 μm is the most prominent and it is not obstructed by spectral features of other substances [C. J. Pouchert, *The Aldrich Library of Infrared Spectra*, 3rd. ed., Aldrich Chemical Co. (1981)] (FIG. 2). The principle of the WM-DPTR method consists in phase-sensitive measurements of oscillating IR radiation emitted by a laser-heated tissue specimen at two discrete wavelengths (at the peak and off-peak of glucose absorption) and relating the observed phase shift to changes of glucose concentration. Dual wavelength detection is required to ensure selectivity of measurements. In our studies, the radiometric signals will be recorded at the peak of the glucose absorption (9.6 μm) and at the reference wavelength of 10.5 μm, near the minimum of glucose absorption (FIG. 2) to isolate the glucose contributions from contributions of water and other tissue substances. To create periodic thermal sources (thermal waves) near the tissue surface, intensity-modulated laser radiation is considered. A theoretical analysis of the thermal wave generation and IR emission can be given using a one-dimensional heat conduction equation in frequency domain [A. Mandelis, *J. Appl. Phys.* 78, 647 (1995); A. Mandelis, *Diffusion-Wave Fields. Mathematical Methods and Green Functions* (New York: Springer, 2001) p. 3] with a harmonic laser-induced heat source following optical absorption at wavelength $\lambda_{IR1}$ with tissue absorption coefficient $\alpha(\lambda_{IR1})$:

$$Q(z,\omega) = \alpha(\lambda_{IR1}) I_0 e^{-\alpha(\lambda_{IR1})z} \cdot e^{i\omega t} \quad (1)$$

where $I_0$(W/cm$^2$) is the laser radiation intensity entering a sample, and $\omega$ is the angular frequency of laser modulation. The harmonic component of the spatial temperature distribution $\tilde{T}(z, \omega)$ and the resulting increase in IR radiometric flux $\tilde{R}(\lambda_{ir}, \omega)$ detected at the wavelength $\lambda_{ir}$ within a narrow spectral band $\delta_\lambda$ can be written as:

$$\tilde{T}(z, \omega) = \frac{\alpha I_0}{\kappa(\sigma^2 - \alpha^2)} \left[ e^{-\alpha z} - \frac{\kappa\alpha + h}{\kappa\sigma + h} e^{-\sigma z} \right] \quad (2)$$

$$\tilde{R}(\lambda_{ir}, \omega) = \left( \frac{\partial M(\lambda_{ir}, T_0)}{\partial T} \right) \frac{\delta_\lambda \alpha_{ir} \alpha I_0}{\kappa(\sigma^2 - \alpha^2)} \left[ \frac{1}{\alpha + \alpha_{ir}} - \frac{\kappa\alpha + h}{\kappa\sigma + h} \cdot \frac{1}{\sigma + \alpha_{ir}} \right] \quad (3)$$

where $M(\lambda_{ir}, T_0)$ is the Plank distribution function for blackbody radiation at the ambient temperature $T_0$, $\kappa$ is the thermal conductivity of tissue, $\sigma(\omega) = \sqrt{i\omega/D}$ is the complex thermal wavenumber; D is tissue thermal diffusivity; the coefficient h describes convective heat loss at the air-tissue interface. Equation (3) shows that the radiometric response $\tilde{R}(\lambda_{ir}, \omega)$ depends on absorption coefficients $\alpha(\lambda_{IR1})$ at the excitation wavelength and $\alpha(\lambda_{ir})$ at the detection wavelength (ca. 5 μm). Therefore, spectroscopic data can be obtained from radiometric measurements if the IR signal is recorded at different excitation wavelengths. The dual wavelength WM-DPTR technique records radiometric signals obtained at $\lambda_{IR1}$, =9.6 μm and $\lambda_{IR2}$=10.5 μm. The response at each wavelength is detected at the same spectral bandwidth ($\lambda_{ir}\delta_\lambda$). A narrowband signal processing algorithm (lock-in) computes the corresponding phases and the differential phase is related to glucose concentration in a tissue specimen. Quantitative estimates of the radiometric signal amplitude and phase can be done using optical properties of human skin assuming water content approximately 70%. The effect of glucose concentration on the absorption coefficient at 9.6 μm was investigated recently [W. B. Martin, S. Mirov and R. Venugopalan, *J. Biomed. Opt.* 7, 613 (2002)]. It was shown that the peak absorption coefficient $\lambda_{IR1}$ depends linearly on glucose concentration, $c_g$, in the range 0-500 mg/dl with slope $d\alpha_{IR1}/dc_g \approx 4.2 \times 10^{-2}$ cm$^{-1}$/(mg/dl). At the same time, the baseline absorption coefficient $\alpha_{IR2}$ is unaffected by glucose. Using, this value of the slope to model linear variations of the absorption coefficient $\alpha(\lambda_{IR1}) = \alpha_{IR1}$ as:

$$\alpha_{IR1}(c_g) = \alpha_{IR1}(c_g = 0) + \left( \frac{d\alpha_{IR1}}{dc_g} \right) \cdot c_g \quad (4)$$

where glucose-free absorption coefficient is taken $\alpha_{IR1}$ ($c_g$=0)= 598 cm$^{-1}$. The differential phase of radiometric signals at the two wavelengths computed for different values of the absorption coefficient, corresponding to a possible maximum and a minimum value of the glucose peak, is shown in FIG. 3. This plot shows a linear increase of differential phase with increase of glucose concentration, however sensitivity (slope of straight lines) is greater for the strong light absorption ($\alpha_{IR1}$=1.24×10$^4$ cm$^{-1}$). Estimates of the differential phase sensitivity suggest that glucose concentration increase of $\Delta c_g$=100 mg/dl should result in the relative phase shift $\Delta\phi \approx 1.4 \times 10^{-3}$ rad for superficial light absorption in tissue. This amounts to a 0.1° phase resolution, which should be quite feasible with today's lock-in technology. Experimental work [P. Zheng, C. E. Kramer, C. W. Barnes, J. R. Braig and B. B. Sterling, *Diabetes Tech. and Therap.* 2, 17 (2000)] reports differential phase measurements with sensitivity $\Delta\phi \approx 3.5 \times 10^{-6}$ rad/(mg/dl) achieved with a thermoelectric cooler. This degree of sensitivity is approx. two orders of magnitude higher than a low absorption peak with $\alpha_{IR1}$=376 cm$^{-1}$, FIG. 3. Note that this 376 cm$^{-1}$ peak was intentionally underestimated compared to the water background absorption of 640 cm$^{-1}$ at 9.7 μm, so as to be taken as a worst case scenario.

In conclusion, these theoretical estimates demonstrate definite feasibility of the Wavelength-Modulated Differential Laser Photothermal Radiometric technique and of the proposed SGR device to detect variations of glucose concentration typical of diabetes patients, with the model indicating phase resolution requirements of $\Delta\phi \sim 10^{-3}$ rad.

While this apparatus and its application has been described and illustrated with respect to a one particular embodiment, it will be appreciated that numerous embodiments of the instrument may be made without departing from the scope of this invention. Some such alternative components and devices to enhance clinical convenience and applicability have already been suggested in the detailed description of the invention.

Therefore what is claimed is:

1. A glucose detection method comprising the steps of:
   a) providing first and second sources of radiation, said first and second sources generating first and second beams, respectively, wherein said first source of radiation has a wavelength approximately equal to a peak wavelength of a glucose absorption band, and wherein said second source of radiation has a wavelength off of said peak wavelength of said glucose absorption band;
   b) producing a first modulated beam and a second modulated beam by modulating an intensity of said first beam and an intensity of said second beam, respectively; wherein said first and second modulated beams are modulated at a substantially equal frequency, and wherein a phase of said first modulated beam differs from a phase of said second modulated beam by approximately 180 degrees;
   c) substantially equalizing an intensity of said first modulated beam and an intensity of said second modulated beam;
   d) directing said first and second modulated beams to co-linearly irradiate a tissue, e) obtaining a signal by detecting blackbody radiation emission radiated by said tissue with a phase-sensitive detection system comprising a thermal detector, wherein a reference signal for said phase-sensitive detection is provided at said frequency; and f) correlating said signal with a concentration of glucose in said tissue.

2. The method according to claim 1 wherein said first and second sources of radiation each have a wavelength between approximately 8.5 and 10.5 μm.

3. The method according to claim 2 wherein said first source of radiation has a wavelength of approximately 9.6 μm and said second source of radiation has a wavelength of approximately 10.5 μm.

4. The method according to claim 1 wherein said phase-sensitive detection system comprises a lock-in amplifier.

5. The method according to claim 1 wherein said first and second radiation sources are one of lasers and spectrally filtered halogen lamps.

6. The method according to claim 1 wherein said frequency is selected to lie within the range of 0.1 Hz to 10 kHz.

7. The method according to claim 1 wherein said intensity of said first modulated beam and said intensity of said second modulated beam is equalized by one of using a neutral density filter and adjusting a current of one of said sources of radiation.

8. The method according to claim 1 wherein said step of correlating said signal with a concentration of glucose in said tissue comprises comparing said signal with a signal obtained from normal tissue.

9. The method according to claim 1 wherein said modulation is achieved by one of driving said first and second sources of radiation with electrical waveforms, mechanical chopping of said first and second beams, acousto-optic modulating of said first and second beams and electro-optical modulating of said first and second beams.

10. The method according to claim 1 wherein said step of directing said first and second modulated beams to co-linearly irradiate said tissue is performed using one of a beam combiner in combination with a mid-infrared lens and optical fibers fitted with a beam combiner in combination with an optical lens at a tip of each said optical fibers.

11. The method according to claim 1 wherein said step of detecting said emission radiated by said tissue comprises collecting said radiated emission with one of solid angle and reflectivity optimized curved mirrors and a mid-IR collecting fiber optic system.

12. The method according to claim 1 further comprising sending said signal to a computer for recording and processing.

13. An apparatus for detecting glucose, said apparatus comprising:

a) first and second sources of radiation, said sources generating first and second beams, respectively, wherein said first source of radiation has a wavelength approximately equal to a peak wavelength of a glucose absorption band, and wherein said second source of radiation has a wavelength off of said peak wavelength of said glucose absorption band;

b) modulation means for modulating an intensity of said first beam and an intensity of said second beam, wherein said modulation means is configured to modulate said first and second beams at a substantially equal frequency, said modulation means being further configured to produce a difference in phase between said first and second modulated beams of approximately 180 degrees;

c) equalizing means for substantially equalizing a power of said first modulated beam and said second modulated beam;

d) optical means for directing said first and second modulated beams to co-linearly irradiate a tissue, e) collection means for collecting thermal power radiated by said tissue;

f) a phase-sensitive detection system comprising a thermal detector configured to detect said collected thermal power, said phase-sensitive detection system receiving as an input a reference signal at said frequency; and g) means for recording and processing said signal.

14. The apparatus according to claim 13 wherein said first and second sources of radiation each have a wavelength between approximately 8.5 and 10.5 μm.

15. The apparatus according to claim 14 wherein said first source of radiation has a wavelength of approximately 9.6 μm and said second source of radiation has a wavelength of approximately 10.5 μm.

16. The apparatus according to claim 13 wherein said phase-sensitive detection system comprises a lock-in amplifier.

17. The apparatus according to claim 13 wherein said first and second radiation sources are one of lasers and spectrally filtered halogen lamps.

18. The apparatus according to claim 13 wherein said first and second radiation sources are carbon dioxide lasers.

19. The apparatus according to claim 13 wherein said frequency lies within the range of 0.1 Hz to 10 kHz.

20. The apparatus according to claim 13 wherein said equalizing means comprises one of a neutral density filter and an adjustment of a current of one of said sources of radiation.

21. The apparatus according to claim 13 wherein said modulation means comprises one of means for driving said first and second sources of radiation with electrical waveforms, means for modulating a current of said first and second sources of radiation, mechanical choppers adapted to chop said first and second beams, acousto-optic modulators adapted to modulate said first and second beams, and electro-optical modulators adapted to modulate said first and second beams.

22. The apparatus according to claim 13 wherein said optical means comprises one of a beam combiner in combination with a mid-infrared lens, and optical fibers fitted with a beam combiner in combination with an optical lens at a tip of each said optical fibers.

23. The apparatus according to claim 13 wherein said means for recording and processing said signal comprises a computer.

24. The apparatus according to claim 13 wherein said collection means comprises one of solid angle and reflectivity optimized curved mirrors and a mid-IR collecting fiber optic system.

* * * * *